United States Patent
Schaer et al.

[19]

[11] Patent Number: 5,882,333
[45] Date of Patent: Mar. 16, 1999

[54] CATHETER WITH DEFLECTABLE DISTAL SECTION

[75] Inventors: Alan K. Schaer, Los Gatos; Duane Dickens, Fremont, both of Calif.

[73] Assignee: Cardima, Inc., Fremont, Calif.

[21] Appl. No.: 242,549

[22] Filed: May 13, 1994

[51] Int. Cl.⁶ .................................................. A61M 37/00
[52] U.S. Cl. .......................... 604/95; 604/164; 604/585; 604/434
[58] Field of Search .................................. 128/657, 772; 604/95, 164, 280, 281, 282, 114; 600/585, 433, 434, 435

[56] References Cited

U.S. PATENT DOCUMENTS

| | | |
|---|---|---|
| 3,547,103 | 12/1970 | Cook . |
| 4,979,510 | 12/1990 | Franz et al. . |
| 5,318,528 | 6/1994 | Heaven et al. ............................ 604/95 |

FOREIGN PATENT DOCUMENTS

| | | |
|---|---|---|
| 0 274 705 | 12/1987 | European Pat. Off. . |
| 0 573 311 A1 | 12/1993 | European Pat. Off. . |
| 93309452 | 6/1994 | European Pat. Off. . |
| WO/92/14506 | 9/1992 | WIPO . |

*Primary Examiner*—Ronald Stright, Jr.
*Attorney, Agent, or Firm*—Heller, Ehrman, White & McAuliffe

[57] ABSTRACT

An electrophysiology catheter assembly having a deflection mechanism rotatably disposed within an inner lumen of the catheter so that deflection of the deflection mechanism within the inner lumen results in a deflection of the distal portion of the catheter. Rotation of the deflection mechanism within the inner lumen of the catheter allows universal deflection of the distal portion of the catheter about its longitudinal axis. The deflection mechanism may be first rotated and then deflected or it may be first deflected and then rotated in a deflected condition. The catheter shaft does not need to be rotated to change the shape of its distal portion.

22 Claims, 10 Drawing Sheets

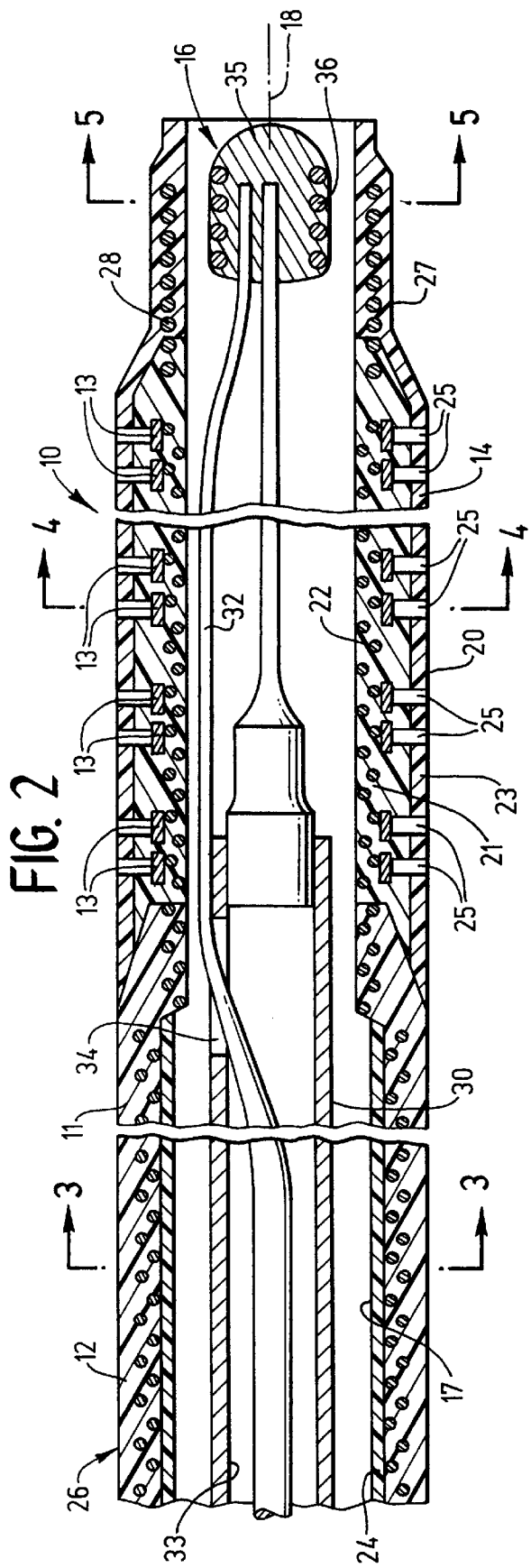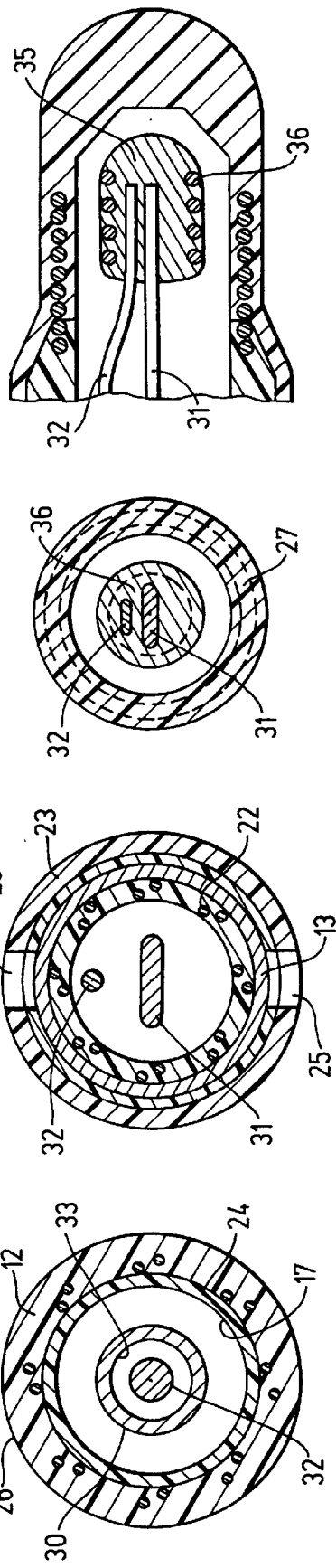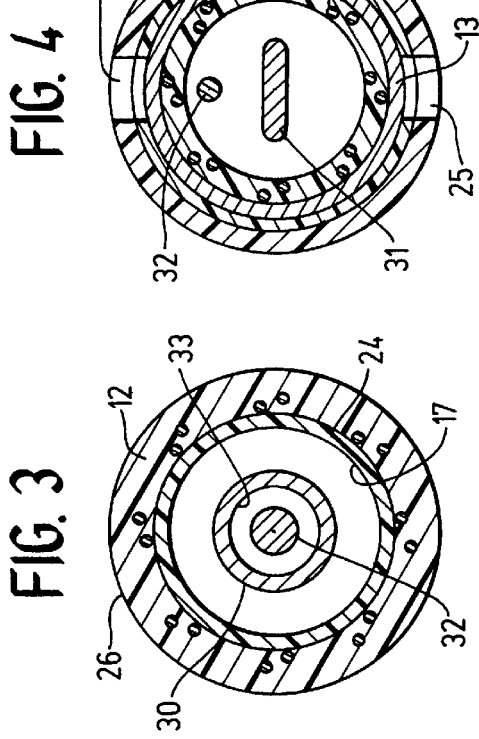

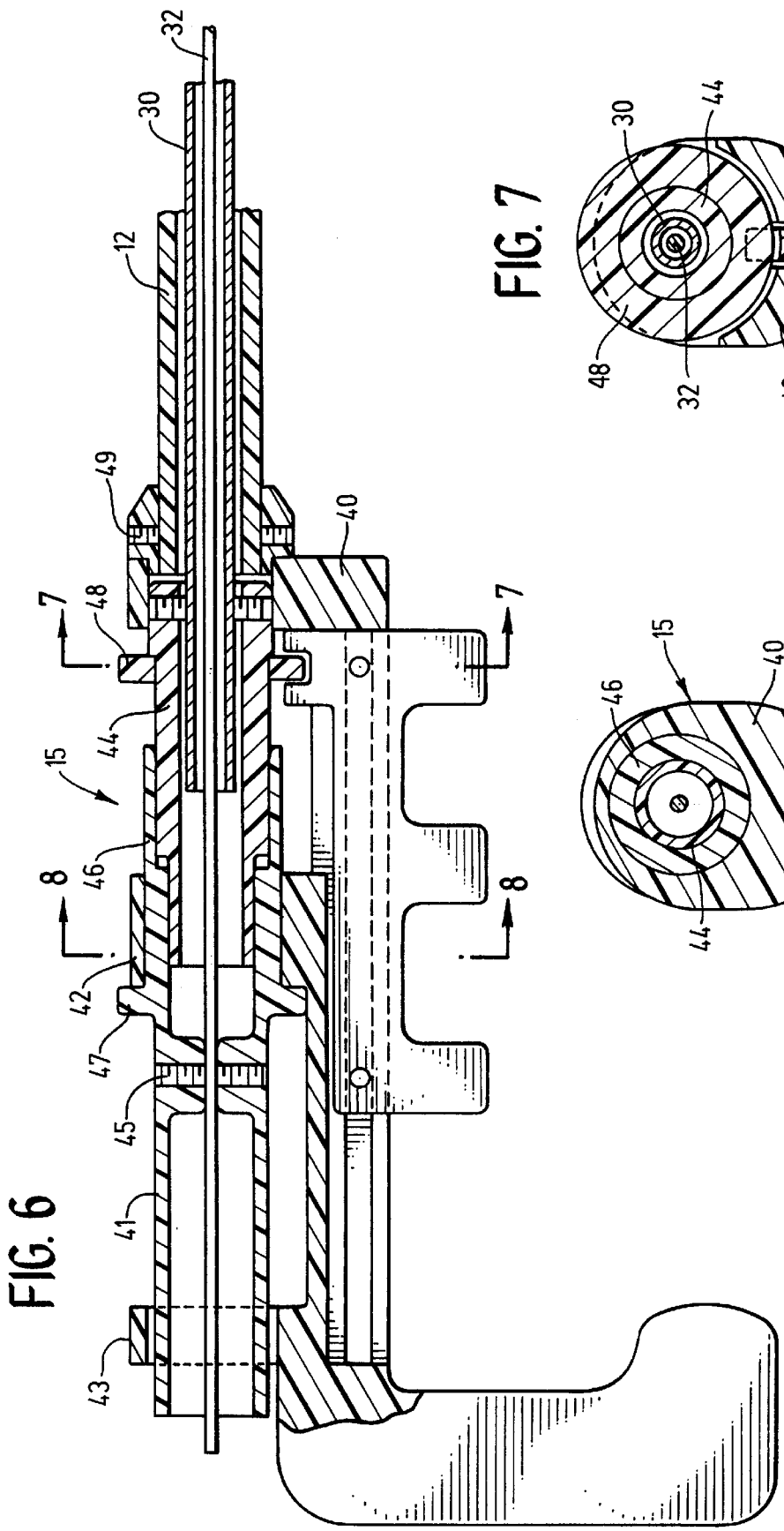

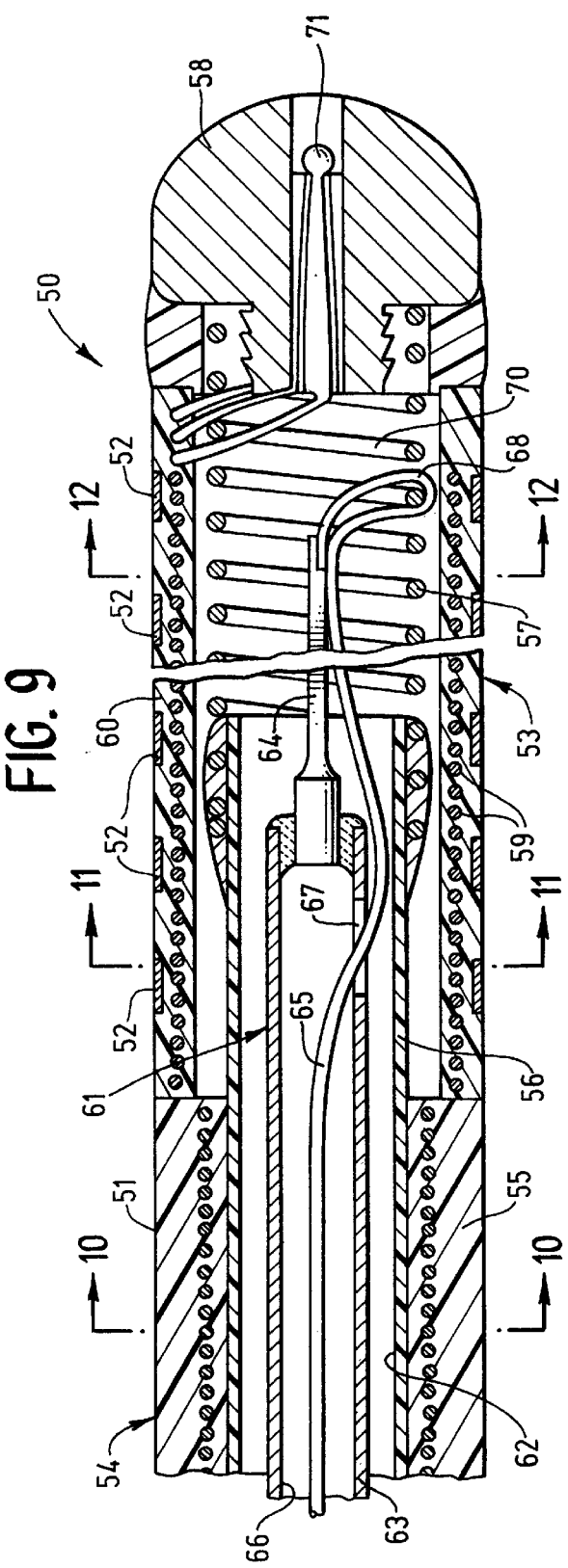
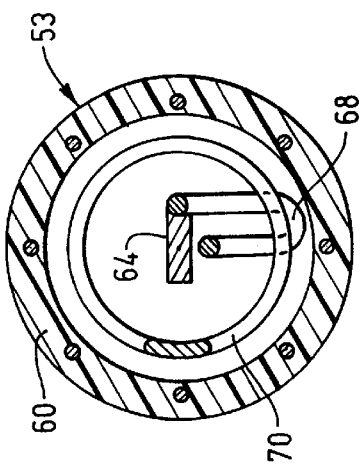
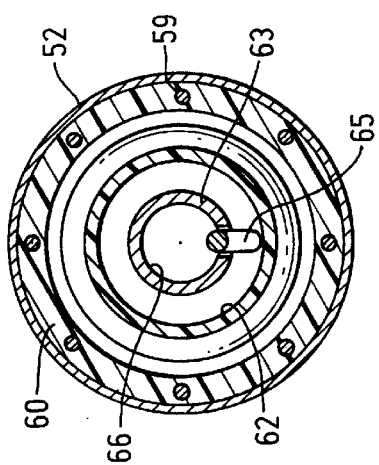
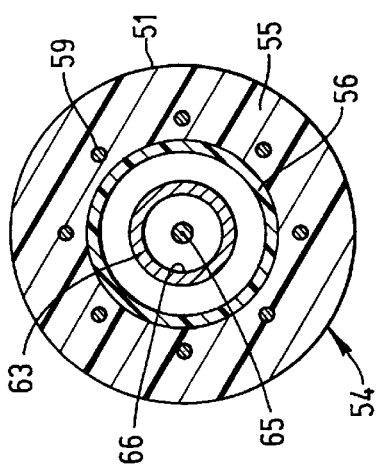

CATHETER WITH DEFLECTABLE DISTAL SECTION

BACKGROUND OF THE INVENTION

This invention relates to intraluminal catheters and particularly to electrophysiology (EP) catheters having distal tips which are shapable after insertion to a patient's body lumen.

EP catheters generally have elongated catheter shafts with one or more electrodes on their distal ends to detect electrical activity or to emit high frequency, e.g. RF, electrical energy, to ablate tissue within a patient's body. Such catheters have been used to detect electrical activity within a patient's heart to determine the location of tissue causing arrhythmia, and to ablate tissue causing arrhythmia once the location of the tissue causing the arrhythmia has been determined.

The distal extremities of EP catheters frequently need to be deflected or shaped within the patient in order to guide the distal extremity into a desireable body lumen or chamber. For example, it is very difficult to advance an EP catheter into a patient's coronary sinus from the inferior vena cava. In other instances it is desireable to shape the distal extremity of an EP catheter to more closely conform the shape of the distal extremity to the patient's endocardium when detecting electrical activity. It is also desireable to shape the distal extremity of an ablation type catheter to orient the distal tip thereof with respect to tissue, such as a patient's endocardium, to facilitate proper delivery of RF energy, laser energy and the like. U.S. Pat. No. 5,190,050 (Nitzche) is an example of an EP type catheter with a deflectable distal tip.

The prior catheters which have a deflection mechanism are usually limited to uniplanar deflection which requires the catheter shaft to be rotated from its proximal end located outside of the patient in order to place the deflected tip into a desired plane, e.g. to seat the distal tip of the catheter into a desired branch of a blood vessel. Unfortunately, the torque applied at the proximal end does not always result in the same rotation at the distal end. Frequently, the catheter shaft will store up the torque and then suddenly release the stored up torque, causing the distal end to suddenly rotate, i.e. whip. Providing a catheter shaft with sufficient strength to transmit to the distal end torque which is applied to the proximal end can increase the stiffness of the shaft to the extent that advancement through tortuous anatomy is difficult.

What has been needed and has heretofore been unavailable is an EP type catheter which has a distal tip with the capability for universal deflection from its longitudinal axis without requiring the entire catheter to be rotated from its proximal end. The present invention satisfies these and other needs.

SUMMARY OF THE INVENTION

The present invention is directed to a catheter assembly having a distal extremity which is universally deflectable from its longitudinal axis.

The catheter assembly of the invention comprises an elongated catheter shaft with an inner lumen extending therein and an elongated deflection mechanism, which is operable from the proximal end of the assembly, disposed within the inner lumen of the catheter shaft and configured to be rotated within the inner lumen.

In a presently preferred embodiment of the invention, the catheter of the assembly is an EP type catheter with one or more electrodes on the distal extremity of the catheter shaft and one or more electrical conductors which are electrically connected to the electrodes on the distal extremity and extend to the proximal end of the catheter shaft. Desirably, the catheter shaft is formed at least in part by the electrical conductors which are wound or braided into a tubular structure. An inner lining may be provided within the tubular structure to define the inner lumen extending within the catheter shaft. An exterior jacket or coating of suitable polymeric material may be applied to the outer surface of the tubular structure to provide a smooth exterior.

The deflection mechanism includes an elongated tubular member with an inner lumen which extends to its distal end and a deflectable element secured to the distal end of the tubular member. A control line, which preferably is slidably disposed within the inner lumen of the tubular member and extends out a port adjacent to the distal end of the tubular member, has its distal end secured to the deflectable element. The proximal end of the control line extends is secured to means for applying tension to effect the deflection of the deflectable element on the distal end of the tubular member and, particularly, to vary the radius of curvature thereof. Deflection of the deflectable element within the inner lumen of the catheter results in the deflection of the catheter shaft. Means are also provided on a proximal portion of the tubular member to rotate the deflection mechanism within the inner lumen of the catheter shaft to facilitate universal deflection of the catheter shaft about its longitudinal axis without the need to rotate the catheter. Rotation of the deflection mechanism within the inner lumen of the catheter shaft can be effected before or after the deflectable distal tip of the deflection mechanism is put into a deflected condition.

The deflection mechanism is preferably configured to be longitudinally slidable within the inner lumen of the catheter shaft so that the location of the catheter shaft deflection can be varied along a length of the catheter shaft.

These and other advantages of the invention will become more apparent from the following detailed description thereof when taken in conjunction with the accompanying exemplary drawings.

BRIEF DESCRIPTION OF THE DRAWINGS

FIG. 2 is a longitudinal cross-sectional view of the distal extremity of the catheter shown in FIG. 1.

FIG. 2A is a longitudinal cross-sectional view of the distal extremity of the catheter similar to that shown in FIG. 2 with a closed distal end.

FIG. 3 is a transverse cross-sectional view of the catheter shown in FIG. 2 taken along the lines 3—3.

FIG. 4 is a transverse cross-sectional view of the catheter shown in FIG. 2 taken along the lines 4—4.

FIG. 5 is a transverse cross-sectional view of the catheter shown in FIG. 2 taken along the lines 5—5.

FIG. 6 is a longitudinal cross-sectional view of the operating handle on the proximal end of the catheter shown in FIG. 1.

FIG. 7 is a transverse cross-sectional view of the handle shown in FIG. 6 taken along the lines 7—7.

FIG. 8 is a transverse cross-sectional view of the handle shown in FIG. 6 taken along the lines 8—8.

FIG. 9 is an elevational view, partially in section, of the distal extremity of an alternative embodiment of the invention.

FIG. 10 is a transverse cross-sectional view of the alternative embodiment shown in FIG. 9 taken along the lines 10—10.

FIG. 11 is a transverse cross-sectional view of the alternative embodiment shown in FIG. 9 taken along the lines 11—11.

FIG. 12 is a transverse cross-sectional view of the distal extremity of the alternative embodiment shown in FIG. 9 taken along the lines 12—12.

DETAILED DESCRIPTION OF THE INVENTION

Figure 1:
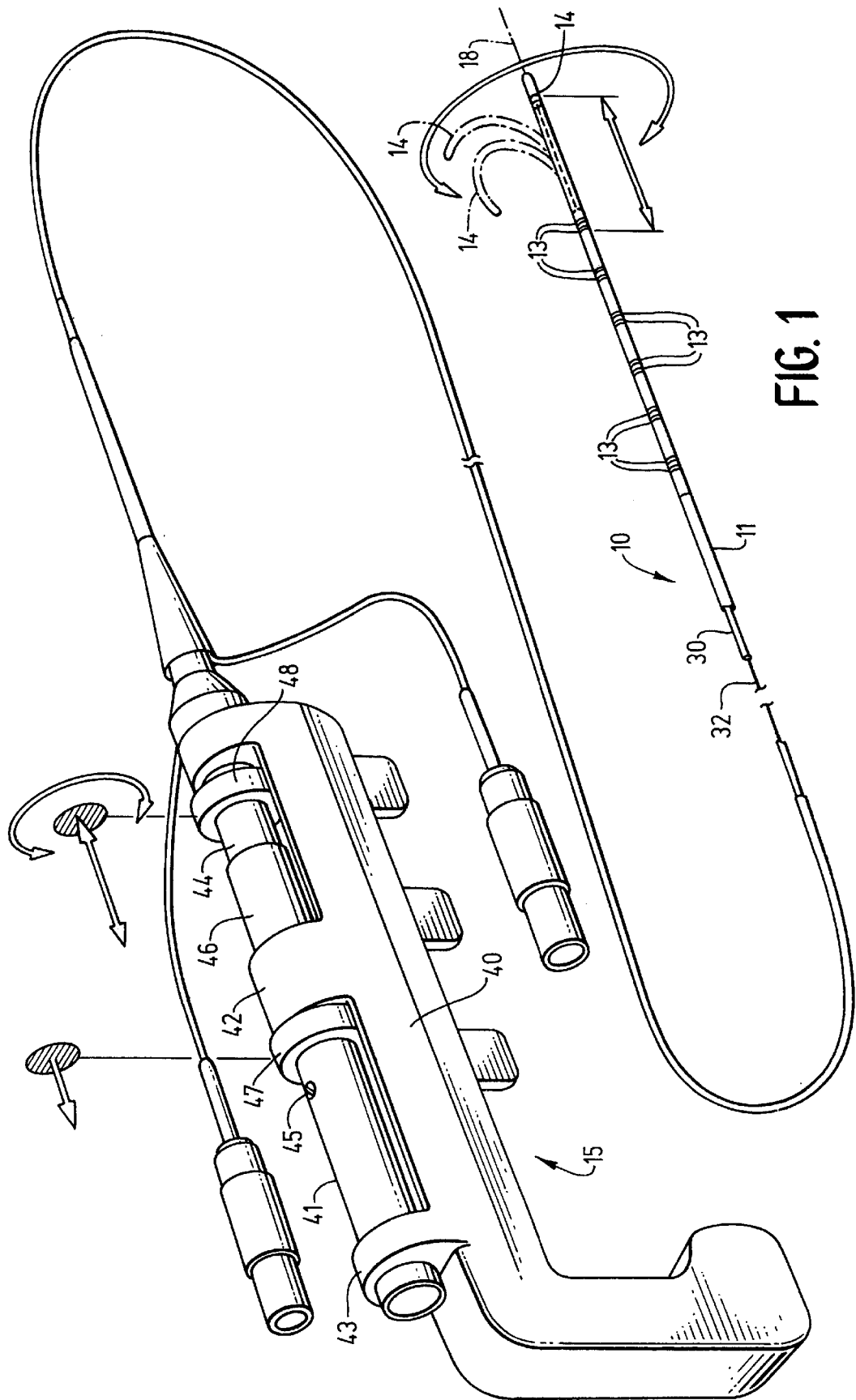
FIG. 1 is a perspective view of an EP type catheter embodying features of the invention.

FIGS. 1–3 illustrate a catheter assembly 10 embodying features of the invention including a catheter 11 which has an elongated shaft 12, a plurality of electrodes 13 on the distal portion 14 of the shaft and an operating handle 15 on the proximal end of the catheter shaft for manipulation of the deflection mechanism 16 which is at least rotatably disposed within the inner lumen 17 of the shaft. The deflection of the distal shaft portion 14 and the rotation of the deflected shapes of the distal shaft portion which are effected by the manipulation of the operating handle 14 on the proximal end of the catheter shaft are illustrated in phantom in FIG. 1. Note that while the deflected shape of the distal shaft portion 14 rotates about the longitudinal axis 18 of the shaft 12, the catheter shaft 12 itself does not rotate.

The distal shaft portion 14, which is shown in greater detail in FIG. 2, has an outer tubular member 20 and a deflection mechanism 16 which is rotatably disposed within the inner lumen 17. The outer tubular member 20 comprises in part a tubular structure 21 formed from a plurality of insulated electrical conductors 22 which are preferably braided into the tubular structure and electrically connected to the electrodes 13 by means of solder or the like (not shown). The electrodes 13 are preferably arranged in pairs as indicated to facilitate a bipolar mode of electrical activity detection. The outer tubular member 20 includes an outer plastic jacket 23, preferably formed of radiopaque plastic materials to provide a smoother exterior and added rigidity, and an inner liner 24 which defines the inner lumen 17. Holes are provided in the jacket 23 to expose the electrodes 13. The distal shaft portion 14 has a smaller diameter than the proximal shaft portion 26 and has a softer and more flexible distal tip 27. A radiopaque coil 28 may be incorporated within the distal tip 27 to facilitate fluoroscopic observation when the elongated catheter assembly 10 is disposed within a patient. The proximal shaft portion 25 may be a continuation of the distal shaft portion 14 or it may be a separate piece and secured to the distal shaft portion.

The deflection mechanism 16, which is rotatably disposed within the inner lumen 17, includes a high strength tubular member 30, a distal deflectable element 31 secured by its proximal end within the distal end of the high strength tubular member, and a deflection control line 32, e.g. cable, wire, or ribbon is slidably disposed within the inner lumen 33 of the high strength tubular member, extends out the port 34 in the wall of the tubular member and is secured by its distal end to the distal end of the deflectable element 31 by means of a body of solder 35. The deflectable element is generally rectangular in transverse cross-section as shown in FIG. 4 and may be tapered along its length in the distal direction. The taper may be in just the short transverse dimension or both the short and long transverse dimensions. It is preferred to provide a radiopaque coil 36, as shown within the body of solder 35, to facilitate the fluoroscopic observation of the distal tip of the deflectable element 31 when the catheter assembly 10 is disposed within a patient. Tension applied to the deflection control line 32 will deflect the deflectable element 31 which in turn deflects the distal shaft portion 14 of the catheter shaft 12 as shown in phantom in FIG. 1. The radius of curvature of the distal shaft section 14 deflected away from the longitudinal axis 18 is controlled by the tension applied to the control line 32. Rotation of the deflection mechanism 16 within the inner lumen 17 of the catheter shaft 12 allows for the universal deflection of the distal shaft portion 14 of the catheter without rotation of the catheter shaft. The deflectable element 31 may also be rotated in a deflected condition to cause the rotation of the deflected shape imposed upon the distal shaft portion 14 by the internal deflection mechanism 16 as indicated in FIG. 1 in phantom. Longitudinal movement of the deflection mechanism 16 within the inner lumen 17 of the catheter shaft 12 allows the deflection of the deflectable element 31 to occur at various locations along a length of the distal shaft portion 14.

As best shown in FIGS. 1, 6, and 7, the operating handle 14 secured to the proximal end of the catheter shaft 12 comprises housing 40, a pull rod 41 slidably disposed within the interior of the housing and supported therein by distal journal 42 and proximal journal 43 and torque rod 44. A proximal extremity of the control line 32 is secured within the pull rod by means of setscrew 45. The distal end of the pull rod 41 is secured within a sheath or guide tube 46 which is configured to be slidably received within the distal journal 42 and to slidably receive the torque rod 44. The pull rod 41 is provided with a thumbwheel 47 to facilitate longitudinal movement of the pull rod within the housing 40 which in turn applies or releases tension to the control line 32 to control the deflection of the deflectable element 31 on the distal extremity of the deflection mechanism 16. Thumbwheel 47 also allows for rotation of the pull rod 41 which is torsionally coupled to the torque rod 44. The torque rod 44 has a flattened proximal portion which is received within a slot within the distal portion of the pull rod 41 and a thumbwheel 48. The proximal end of the catheter shaft 12 is secured to the distal end of the housing 40 by means of a set screw 49 or other suitable means. Rotation of the thumbwheel 48 rotates the torque rod 44 within the inner lumen 17 of the catheter shaft 11. If the pull rod 41 has been pulled proximally so as to deflect the deflectable element 31 on the distal end of the torque tube 30, turning the thumbwheel 48 will rotate the deflected tip within the inner lumen 18 and rotate the deformed distal shaft portion 13 as indicated in FIG. 1. Longitudinal movement of the thumbwheel 48 will move the deflection mechanism 16 longitudinally within the inner lumen 17.

An alternative embodiment of the invention is partially illustrated in FIGS. 9–12. In this embodiment, the catheter assembly 50 has a catheter shaft 51 with a plurality of electrodes 52 on the distal shaft portion 53. The proximal portion 54 of the catheter shaft 51 has an outer tubular member 55 and a inner tubular member 56 which is secured to the outer tubular member by a suitable adhesive (e.g. an epoxy). A flexible expanded coil 57 is secured by its proximal end to the distal end of the inner tubular member 56, which extends into the distal shaft portion 53, and by its distal end to a distal tip electrode 58 formed of solder which may be either a sensing or emitting electrode. In the distal shaft portion 53, a plurality of electrical conductors 59 are braided or wound into a tubular shape and incorporated into a polymeric tube 60 upon which the electrodes 52 are mounted. Each electrode 52 is electrically connected to at least one conductor 59 by means of solder or other suitable electrical connection. One or more of the conductors 59 are also electrically connected to the distal tip electrode 58 which may be a sensing or emitting electrode. The distal end of the polymeric tube 60 is secured to the distal tip electrode 58 by means of an adhesive (e.g. epoxy) and the proximal end is secured by adhesive to the outer tubular member 55. The deflection mechanism 61, which is rotatably disposed within the inner lumen 62 of the inner tubular member 56, includes a torque tube 63, a deflectable element 64 and a control line 65 which is slidably disposed within the inner lumen 66 of the torque tube. The control line 65 extends out port 67 in the distal extremity of the torque tube 63 and is secured to the distal tip of the deflectable element 64 by solder or a suitable adhesive. The control line 65 is provided with a loop 68 which is disposed about the wire 70 forming the coil 57.

The application of tension to the control line 65 will deflect the deflectable element 64 as in the prior embodiment. Rotation of the torque tube 63 within the inner lumen 64 will cause the loop 68 of the control line 65 to ride along the wire 70 forming the coil 57 so as to longitudinally move the deflection mechanism 61 within the inner lumen 62 of the inner tube 56.

In the embodiment shown in FIGS. 9–12 a thermistor 71 is preferably provided in the distal tip electrode but electrically isolated therefrom to detect temperature. The thermistor 71 may be electrically connected to a pair of electrical conductors 59 as shown.

Figure 13:
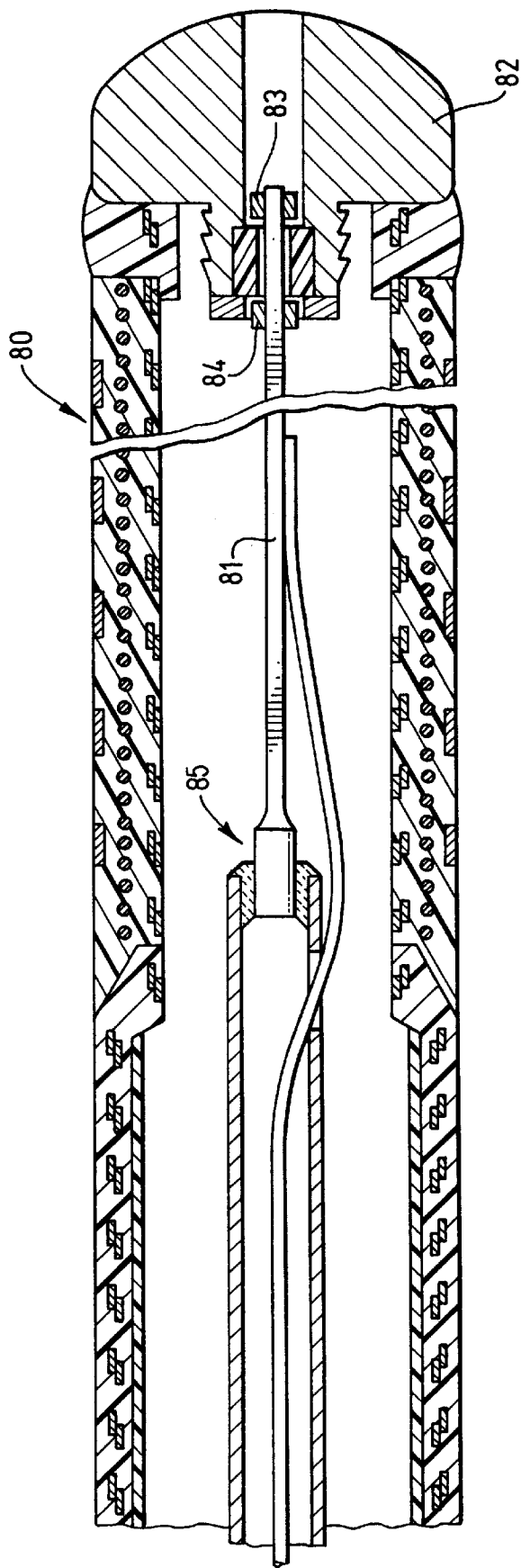
FIG. 13 is an elevational view, partially in section, of the distal extremity of another alternative embodiment of the invention.

Another embodiment of the invention is shown in FIG. 13 wherein the catheter assembly 80 has a deflectable element 81 which is secured to the distal tip electrode 82 by means of collars 83 and 84. The other portions of the catheter assembly 80 are essentially the same as the assembly shown in FIGS. 2–5 except that there is no coil. This embodiment provides more positive control of the distal tip of the catheter and a stronger distal tip electrode than the embodiments previously described. However, it does not allow for the longitudinal movement of the deflectable mechanism 85.

Figure 14:
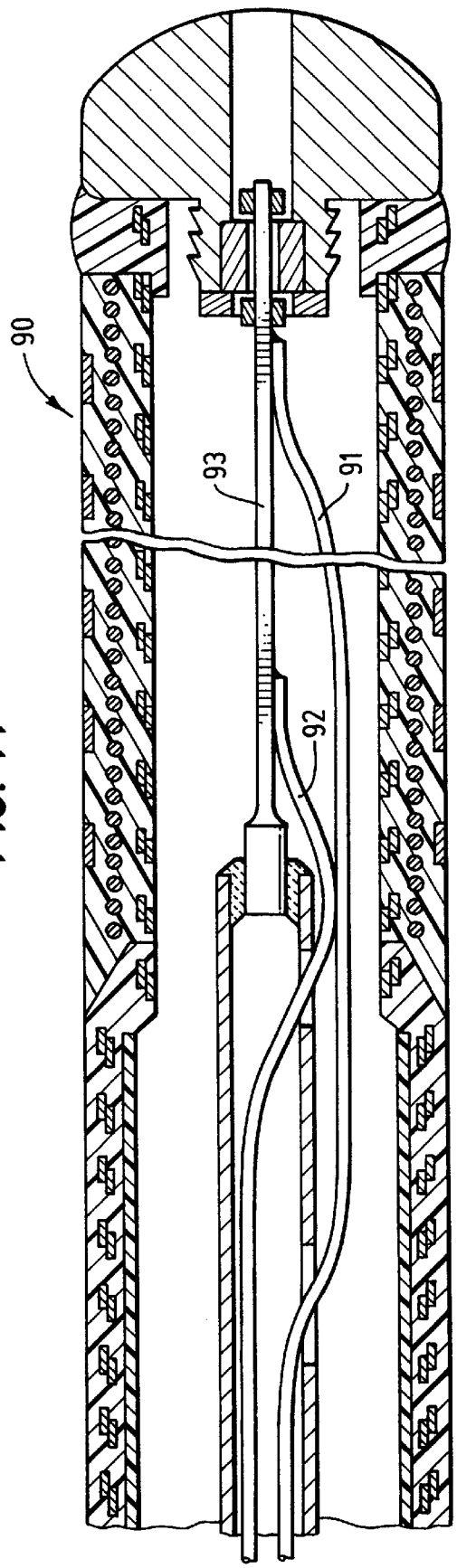
FIG. 14 is an elevational view, partially in section, of the distal extremity of another embodiment of the invention.
Figure 16:
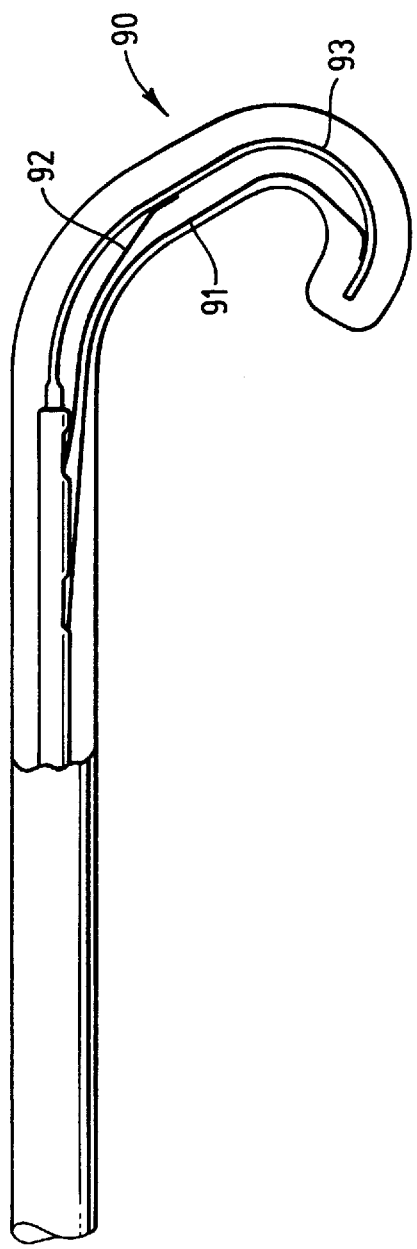
FIG. 16 is an elevational view, partially in section, of the distal extremity of the alternative embodiment shown in FIG. 14 in a deflected condition.

FIG. 14 illustrates another embodiment of the invention wherein catheter assembly 90 has a pair of control lines 91 and 92 which are connected to the deflectable element 93 at different locations along the same side thereof. The catheter assembly 90 is otherwise essentially the same as the embodiment shown in FIG. 9. Tension applied to control lines 91 and 92, either together or independently, allow different curvatures to be formed in the deflectable element 93 along its length as shown in FIG. 16.

Figure 15:
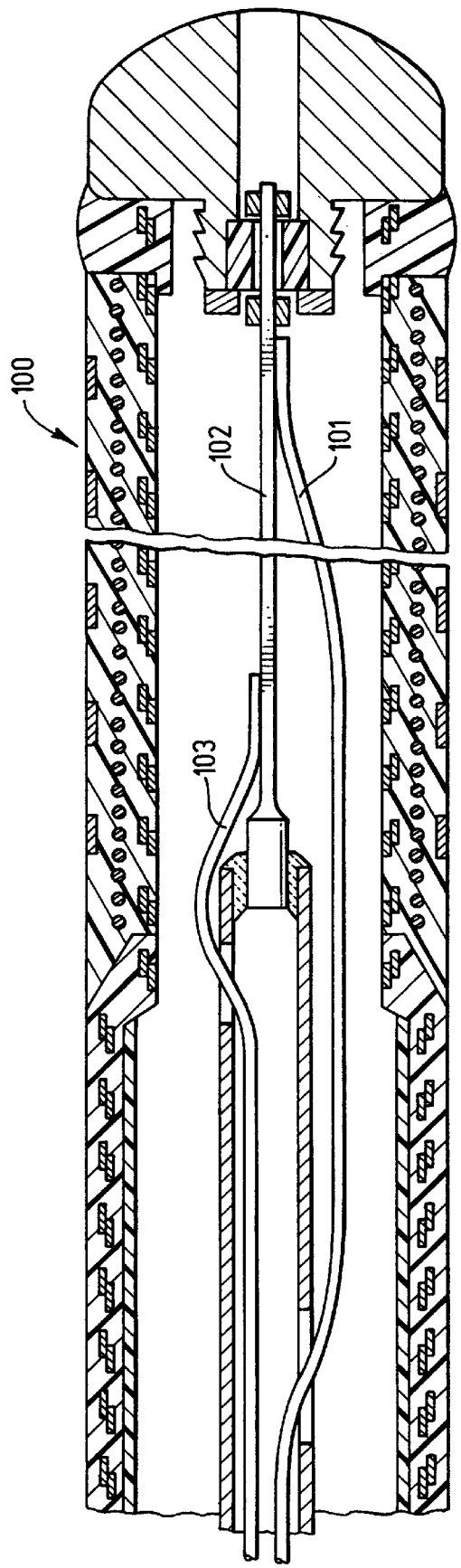
FIG. 15 is an elevational view, partially in section, of the distal extremity of another alternative embodiment of the invention.
Figure 17:
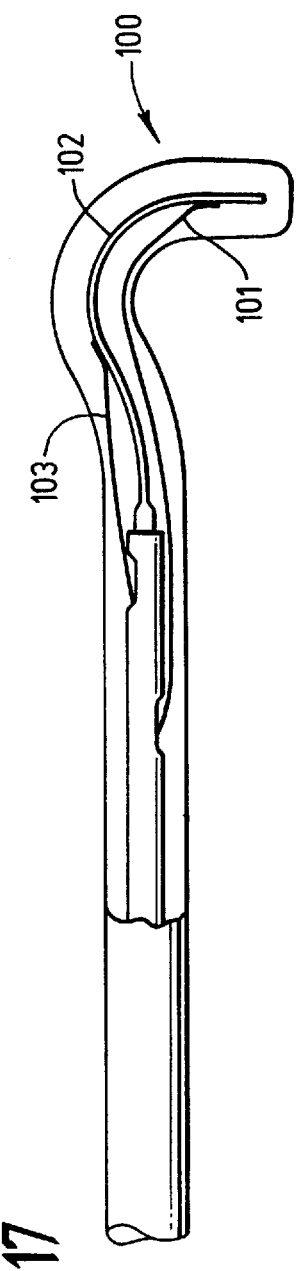
FIG. 17 is an elevational view, partially in section, of the distal extremity of the alternative embodiment shown in FIG. 15 in a deflected condition.

FIG. 15 illustrates yet another embodiment of the invention wherein catheter assembly 100 has one control line 101 connected to a distal portion of the deflectable element 102 and one control line 103 connected to a proximal portion of the deflectable element. As shown in FIG. 17, tension applied to both control lines either together or independently form a variety of curvatures in the deflectable element 102, many of which are not attainable in the embodiment shown in FIG. 14. The catheter assembly 100 is otherwise essentially the same as the embodiment shown in FIG. 9.

Figure 18:
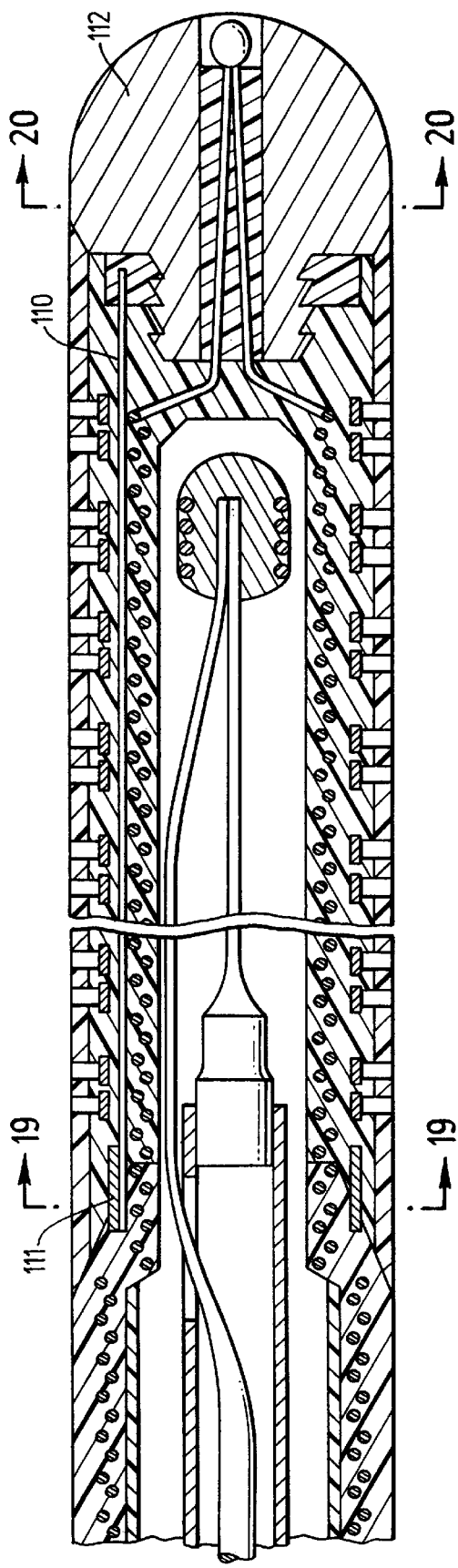
FIG. 18 is an elevational view, partially in section, of the distal extremity of another alternative embodiment of the invention.
Figure 20:
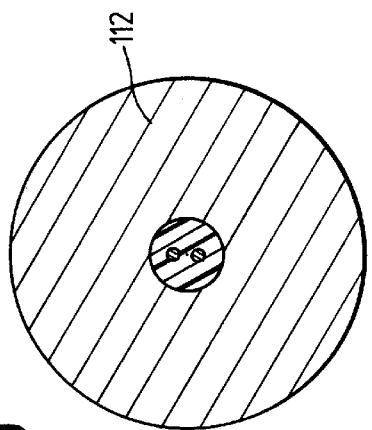
FIG. 20 is a transverse cross-sectional view of the distal extremity of the alternative embodiment shown in FIG. 9 taken along the lines 20—20.
Figure 19:
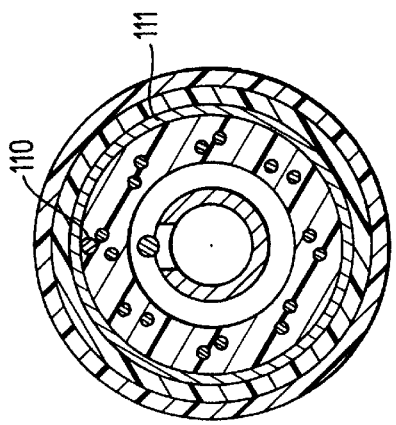
FIG. 19 is a transverse cross-sectional view of the alternative embodiment shown in FIG. 18 taken along the lines 19—19.

FIGS. 18–20 depict another alternative embodiment which has particular utility with an ablation type catheter assembly. In this embodiment a safety wire 110 is provided which has its proximal end secured, e.g. soldered or suitable adhesive, to a cylindrical anchor 111 and its distal end secured in a similar fashion to the distal tip electrode 112 to provide improved tensile strengths of the distal portion and to prevent the distal tip electrode from being pulled off in use. A suitable safety wire is a 0.003 inch (0.076 mm) diameter stainless steel wire with a polyimide jacket.

Figure 21:
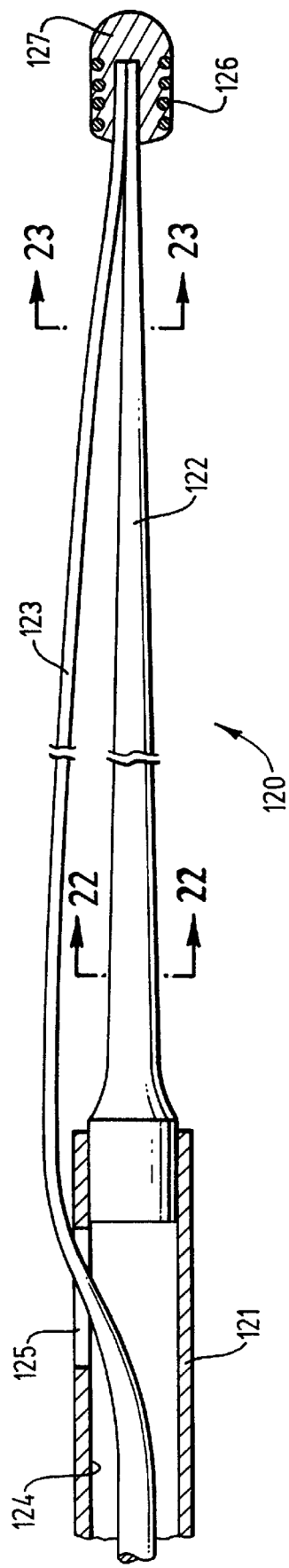
FIG. 21 is an elevational view, partially in section, of an alternative embodiment of a deflection mechanism.
Figure 23:
FIG. 23 is a transverse cross-sectional view of the deflection mechanism shown in FIG. 21 taken along the lines 23—23.
Figure 22:
FIG. 22 is a transverse cross-sectional view of the deflection mechanism shown in FIG. 21 taken along the lines 22—22.

FIGS. 21–23 schematically illustrate an alternative deflection mechanism 120 which includes a high strength tubular member 121 which has a deflectable element 122 secured within the distal end of the tubular member. A control wire 123 extends through the inner lumen 124 in the tubular member 121 and out the port 125 and is secured by its distal end to the thinned portion of deflectable element 122. A helical coil 126 is disposed about the distal extremity of the deflectable element 122 and is secured to the distal end thereof by a body of solder which forms the plug 127 which may also be an electrode as in the previously discussed embodiments. The deflectable element 122, which generally has a rectangular transverse cross-section is tapered in the distal direction to a smaller short transverse dimension to provide greater flexibility along the length of the deflectable element in the direction of the short transverse dimension. The deflectable element 122 may also be tapered distally in the long transverse dimension to provide additional flexibility.

The overall length of the catheter assembly of the invention for use within the vessels or chambers of a patient's heart ranges from about 90 to about 150 cm, preferably about 110 to about 135 cm. Uses in other portions of a patient's body may require other lengths. The outer diameter of the distal portions of the catheters will depend upon their uses but generally will vary from about 0.015 to about 0.08 inch (0.38–2 mm).

The components of the catheter assembly of the present invention may be formed of conventional material. For example the outer tubular member may be formed of polyethylene, a polyester or a polyester-polyamide material such as Hytrel®. The high strength tubular element of the deflection mechanism may be formed of hypotubing of stainless steel or a pseudoelastic NiTi alloy. The control line may likewise be made of stainless steel or a pseudoelastic NiTi alloy.

One presently contemplated use of the catheter assembly of the present invention is for the mapping of electrical activity within a patient's coronary sinus or a vein branched therefrom and within a patient's heart chambers. In this use, the catheter assembly is percutaneously introduced into the patient's femoral vein, advanced through the inferior vena cava into the right atrium. The distal portion of the catheter is usually maintained relatively straight up to this point. Once inside the right atrium, the distal portion of the catheter assembly is deflected by operating the deflecting mechanism to facilitate the introduction of the distal portion of the assembly into the ostium of the patient's coronary sinus. Once inside the coronary sinus the distal portion may be straightened to facilitate passage through the coronary sinus and into the great vein extending therefrom. The distal portion may be deflected again to select a venous branch once inside the coronary sinus or the great vein.

The deflection of the distal portion of the catheter can also be employed to conform the shape of the distal portion to the shape of the inner surface of a heart chamber to more efficiently detect signals by means of the electrodes on the distal portion or to make better contact between a distal tip electrode on the distal portion and the endocardial tissue to be ablated. Other uses will be apparent to those skilled in the art.

While the present invention is described herein in terms of certain presently preferred embodiments, various modifications and improvements can be made to the invention. For example, in the embodiments described herein, the deflectable element is essentially straight and the control line secured thereto is employed to curve or deflect the deflectable element. It is also contemplated to permanently deform or curve the deflectable element before the catheter assembly is introduced into the patient's vasculature and use the control line to hold the deflectable element in a straightened condition while it is being advanced and then releasing the tension applied to the control line when the deflectable element is to assume a deflected or curved shape. Other modifications can be made without departing from the scope thereof.

What is claimed is:

1. An elongated catheter assembly comprising:
   a) an elongated catheter which has proximal and distal sections, an inner lumen extending therein and at least one electrode on a distal portion thereof; and
   b) an internal deflection means disposed within the inner lumen of the catheter which has a deflectable distal tip portion and which is free to axially rotate within the inner lumen of the catheter and with respect to the catheter so that rotation of the internal deflection means within the inner lumen of the catheter will allow the distal portion of the catheter to be deflected about a longitudinal axis of the catheter without axially rotating the catheter.

2. The elongated catheter assembly of claim 1 wherein the elongated catheter has a closed distal tip.

3. The elongated catheter assembly of claim 2 wherein the deflectable distal tip of the internal deflection means is rotatably secured to the closed distal tip of the catheter.

4. The elongated catheter assembly of claim 3 wherein the closed distal tip of the catheter is an electrode.

5. The elongated catheter assembly of claim 4 wherein the electrode is an ablation electrode.

6. The elongated catheter assembly of claim 5 including a temperature sensing means on the distal tip of the catheter.

7. The elongated catheter assembly of claim 4 wherein a safety wire or ribbon which has proximal and distal ends is disposed within the catheter with its distal end secured to the distal tip electrode and its proximal end secured within the catheter at a location proximal to the distal tip electrode.

8. The elongated catheter assembly of claim 7 wherein a ring shaped anchor is provided in the catheter and the proximal end of the safety wire is secured thereto.

9. The elongated catheter of claim 1 wherein the internal deflection means includes a tubular member with proximal and distal ends, an inner lumen extending therein, a port near the distal end thereof in fluid communication with the inner lumen and the deflectable distal tip secured to the distal end of the tubular member and a control wire slidably disposed within the inner lumen of the tubular member extending out the port near the distal end thereof and secured to the deflectable distal tip whereby the application of tension to the control wire causes the deflection of the deflectable distal tip.

10. The elongated catheter assembly of claim 9 wherein the internal deflection means includes a second control wire which is slidably disposed within the inner lumen of the tubular member, which extends out a second port in the tubular member and which is secured the deflectable distal tip at a second location.

11. The elongated catheter assembly of claim 10 wherein the second control wire is secured to the same side of the deflectable distal tip as the first control wire is secured to.

12. The elongated catheter assembly of claim 10 wherein the second control wire is secured to the side of the deflectable distal tip opposite to the side the first control wire is secured to.

13. The elongated catheter of claim 9 wherein the deflectable distal tip of the internal deflection means is unsecured to the catheter.

14. The elongated catheter of claim 13 including a distal end and a port in the distal end.

15. The elongated catheter of claim 13 including a closed distal end.

16. The elongated catheter assembly of claim 9 wherein the internal deflection means includes a helically coiled wire disposed about the deflectable distal tip and wherein the means to longitudinally move the internal deflection means includes a loop which is secured to the deflectable distal tip and which slidably engages the wire forming the helical coil whereby rotation of the internal deflection means about a longitudinal axis thereof causes the longitudinal movement of the internal deflection means within the inner lumen of the catheter.

17. The elongated catheter assembly of claim 9 wherein the deflectable distal tip has a rectangular transverse cross-section.

18. The elongated catheter assembly of claim 9 wherein the deflectable distal tip tapers in the distal direction to a smaller short transverse dimension.

19. The elongated catheter assembly of claim 1 including means operable from the proximal section of the catheter assembly to adjust the deflection of the deflectable distal tip of the internal deflection means.

20. The elongated catheter assembly of claim 1 including means to longitudinally move the internal deflection means within the inner lumen of the catheter independent of the means to deflect the deflectable distal tip thereof.

21. The elongated catheter assembly of claim 1 wherein the deflectable distal tip of the internal defection means is rotatably secured to the distal end of the catheter.

22. An elongated electrophysiology catheter assembly comprising:
   a) an elongated intravascular catheter which has proximal and distal sections, an inner lumen extending therein, a plurality of electrodes on a distal portion thereof and a plurality of electrical conductors, each electrically connected to an electrode; and
   b) an internal deflection means disposed within a deflectable distal tip portion and which is free to axially rotate within the inner lumen of the catheter and with respect to the catheter so that rotation of the internal deflection means within the inner lumen of the catheter will allow the distal portion of the catheter to be deflected about a longitudinal axis of the catheter without axially rotating the catheter.

* * * * *